United States Patent [19]

Fujio et al.

[11] Patent Number: 5,212,079

[45] Date of Patent: May 18, 1993

[54] PROCESS FOR THE PREPARATION OF ASCORBIC ACID-2-PHOSPHATE

[75] Inventors: Tatsuro Fujio; Akihiko Maruyama, both of Kanagawa; Satoshi Koizumi, Tokyo, all of Japan

[73] Assignee: Kyowa Hakko Kogyo Kabushiki Kaisha, Tokyo, Japan

[21] Appl. No.: 758,528

[22] Filed: Sep. 6, 1991

Related U.S. Application Data

[63] Continuation of Ser. No. 642,144, Jan. 15, 1991, abandoned, which is a continuation of Ser. No. 255,182, Oct. 7, 1988, abandoned.

[30] Foreign Application Priority Data

Oct. 8, 1987 [JP] Japan ............................... 62-254106
Mar. 24, 1988 [JP] Japan ............................... 63-70218

[51] Int. Cl.$^5$ ............................................. C12P 9/00
[52] U.S. Cl. .................................... 435/131; 435/170; 435/194; 549/222
[58] Field of Search ..................... 435/131, 170, 194

[56] References Cited

FOREIGN PATENT DOCUMENTS

| 0272064 | 6/1988 | European Pat. Off. ............ 435/128 |
| 289416 | 11/1988 | European Pat. Off. ............ 435/131 |
| 48-15605 | 5/1973 | Japan . |
| 72881 | 6/1977 | Japan ................................. 435/131 |

OTHER PUBLICATIONS

Mitsugi et al., Agr. Biol. Chem., vol. 28, No. 9, pp. 586–600 (1964).
J. Org. Chem. 47, 3453 (1982).

*Primary Examiner*—Carolyn Elmore
*Assistant Examiner*—Shailendra Kumar
*Attorney, Agent, or Firm*—Schweitzer Cornman & Gross

[57] ABSTRACT

A process for the preparation of ascorbic acid-2-phosphate, which comprises reacting ascorbic acid or araboascorbic acid with a phosphate donor other than ATP in an aqueous medium in the presence of an effective amount of an enzyme derived and capable of preferentially catalyzing the enzymatic phosphorylation in the 2-position of ascorbic acid or araboascorbic acid by said phosphate donor, and recovering the resultant ascorbic acid-2-phosphate from the reaction solution.

8 Claims, No Drawings

PROCESS FOR THE PREPARATION OF ASCORBIC ACID-2-PHOSPHATE

This application is a continuation of application Ser. No. 642,144, filed Jan. 15, 1991 (abandoned), a continuation of Ser. No. 255,182, filed Oct. 7, 1988 (abandoned).

FIELD OF THE INVENTION

The present invention relates to a process for the preparation of ascorbic acid-2-phosphate (hereinafter referred to as AsA2P). Ascorbic acid is widely used, for example, in the fields of medicines, foodstuffs and cosmetics but has the disadvantage that it is susceptible to decomposition, for example by exposure to heat, air or light.

BACKGROUND OF THE INVENTION

AsA2P is a stable derivative which is easily converted into ascorbic acid by dephosphorylation in the body and hence exhibits vitamin C activity. AsA2P is therefore widely used, for example, as a raw material for the preparation of cosmetics and medicines, particularly cosmetics, and as an additive to foodstuffs.

Processes for the preparation of AsA2P by chemical synthesis are known [for example, JP-A-30328/70, 15605/73 and 18191/77 and J. Org. Chem. 47, 3453, (1982)]. The use of enzymes of microbial origin for the preparation of AsA2P has been reported in the Abstract of Lectures at the meeting of Japanese Society of Agricultural Chemistry, 4 L-1, p. 696 (1987).

Chemical synthesis has already been used for the preparation of AsA2P on an industrial scale. However, chemical synthesis has the inherent disadvantage that, in addition to the desired phosphorylation at the 2-position, various phosphorylated isomers for example, at the 3- and 6-positions may be inevitably produced and thus it is difficult to obtain a high yield of AsA2P. Consequently, various attempts have been made to improve the production yield of AsA2P, for example, by introducing a protecting group or by selecting the operation conditions. However, the known processes of preparation are still complicated and expensive, and moreover, it is difficult to produce AsA2P with high purity.

In the known preparative method using an enzyme originating from a microorganism of the species Citrobacter freundii (cf. Abstracts of the Lectures at the meeting of Japanese Society of Agricultural Chemistry, 4 L-1, p.696 (1987)), it was reported that, in this case, a major proportion of the product is phosphorylated at the 6-position and that, in order to obtain AsA2P, it is necessary to introduce a protecting group (for example, isopropylidene) before the beginning of the reaction, and then to remove it after the completion of the reaction.

As disclosed in our EP-A-0,272,064, we have previously discovered that various microorganisms are capable of specifically phosphorylating ascorbic acid at the 2-position to form AsA2P in the presence of ATP.

THE INVENTION

The drawback of the above process is the high cost of ATP. We have now found that certain microorganisms are capable of specifically phosphorylating ascorbic acid at the 2-position, in the presence of simpler and cheaper phosphate donors, for example, pyrophosphoric acid.

Thus, in one aspect, our invention provides a process for the preparation of ascorbic acid-2-phosphate, which comprises reacting ascorbic acid or araboascorbic acid with a phosphate donor other than ATP in an aqueous medium in the presence of an effective amount of an enzyme derived from a microorganism and capable of preferentially catalyzing the enzymatic phosphorylation in the 2-position of ascorbic acid or araboascorbic acid by said phosphate donor, and recovering the resultant ascorbic acid-2-phosphate from the reaction solution.

It will be understood that the term ascorbic acid includes both D- and L-isomeric forms of ascorbic acid.

DETAILED DESCRIPTION

Examples of the phosphate donors which may be used include non-nucleotide phosphate esters, especially substituted phenyl phosphates such as paranitrophenylphosphate; mixed anhydrides of phosphoric acid e.g. with lower carboxylic acids, such as acetylphosphoric acid; and condensed or polymerised phosphoric acids such as pyrophosphoric acid, tripolyphosphoric acid, tetrapolyphosphoric acid and polyphosphoric acid.

The microorganisms, which may be used for the purpose of the present invention, include those capable of producing the AsA2P from ascorbic acid or araboascorbic acid and a phosphate donor; belonging to the genera Klebsiella, Cellulomonas, Alcaligenes, Aeromonas, Brevibacterium, Pseudomonas, Flavobacterium, Xanthomonas, Morganella, Serratia, Enterobacter, Bacillus and Corynebacterium.

Examples of suitable microorganisms include

| | | |
|---|---|---|
| Klebsiella oxytoca | ATCC | 8724 |
| Cellulomonas flavigena SK-4 | FERM-BP | 1575 |
| Cellulomonas cartae | ATC | 21681 |
| Alcaligenes eutrophus | ATCC | 17697 |
| Beneckea hyperoptica | ATCC | 15803 |
| Aeromonas hydrophila | ATCC | 11163 |
| Klebsiella pneumoniae | ATCC | 21524 |
| Brevibacterium lyticum | ATCC | 15921 |
| Brevibacterium ammoniagenes | ATCC | 6872 |
| Brevibacterium flavum | ATCC | 13826 |
| Brevibacterium lactofermentum | ATCC | 13655 |
| Pseudomonas riboflavina | ATCC | 9526 |
| Pseudomonas diminuta | ATCC | 11568 |
| Flavobacterium devorans | ATCC | 10829 |
| Pseudomonas azotocolligans | ATCC | 12417 |
| Pseudomonas maltophilia | ATCC | 17806 |
| Xanthomonas oryzae | IFO | 3995 |
| Morganella morganii | ATCC | 25830 |
| Serratia rubidaea | ATCC | 11634 |
| Enterobacter aerogenes | ATCC | 13048 |
| Bacillus subtilis | ATCC | 19221 |
| Corynebacterium glutamicum | ATCC | 13032 |

It is possible to culture the microorganisms using conventional media, for example, KM102 medium containing polypeptone (10 g/o), meat extract (7 g/l), yeast extract (5 g/l) and sodium chloride (3 g/l) and having an adjusted pH of 7.2, provided the microorganisms used as capable of growing well without inhibition of their ability to produce AsA2P. It is also possible to use various organic, semi-synthetic and synthetic media containing sources of carbon and nitrogen and other inorganic and/or organic substances.

Preferred carbon sources include, for example, carbohydrates such as glucose, fructose, sucrose, or maltose; sugar alcohols such as mannitol or sorbitol; alcohols such as glycerol; organic acids such as pyruvic acid, lactic acid or citric acid; and amino acids such as glutamic acid, methionine, or lysine. If desired, other naturally-occurring organic nutrients such as starch hydrolyzate, molasses, waste molasses, white rice bran, cassava, bagasse or corn steep liquor may be used.

Examples of nitrogen sources include inorganic and organic salts of ammonium such as urea, ammonia, ammonium chloride, ammonium sulfate, ammonium carbonate or ammonium acetate; amino acids such as glutamic acid, glutamine or methionine; and nitrogen-containing organic material such as peptone, ZN amine, corn steep liquor, meat extract, yeast extract, casein hydrolyzate, fish meal and digested products thereof or chrysalis hydrolyzate.

Examples of inorganic substances include dibasic potassium phosphate, monobasic sodium phosphate, magnesium sulfate, sodium chloride, calcium chloride, iron chloride, copper sulfate, manganese chloride, ammonium molybdate and zinc sulfate, of which suitable amounts may be added to the medium.

Vitamins, amino acids, nucleic acids and other substances which may be required for the growth of microorganisms may, if desired and if necessary, be added to the medium.

It is preferred to carry out the culturing under aerobic conditions, for example, with shaking or with aeration and agitation. Usually the culturing may be effected at a temperature of from 20° to 40° C., preferably from 25° to 35° C. and at a pH of from 4 to 10, preferably from 6.5 to 7.5 for a period of 1 to 100 hours.

AsA2P is formed by the reaction of ascorbic acid or araboascorbic acid with a phosphate donor. The reaction may be carried out by one of the following methods:

(1) combining ascorbic acid or araboascorbic acid with a phosphate donor in the culture broth of a microorganism; or (2) mixing at least one member selected from a culture broth, microbial cells, supernatant of a culture broth and products obtained by treatment thereof, with a solution containing ascorbic acid or araboascorbic acid and a phosphate donor, other than ATP.

Additives such as surfactants or organic solvents may, if desired, be added to the reaction solution to increase the production yield of AsA2P.

Suitable surfactants include, for example, cationic surfactants such an polyoxyethylene stearylamine (for example, Nymin S-215, commercial product of Nihon Yushi K. K., Japan), or cetyltrimethylammoniumbromide; anionic surfactants such as sodium oleylamide sulfate; and amphoteric surfactants such as polyoxyethylenesorbitan monostearate (for example, Nonion ST 221, commercial product of Nihon Yushi K. K., Japan), which are capable of promoting the reaction to produce AsA2P from ascorbic acid or araboascorbic acid and a phosphate donor. Usually, the surfactant may be used in an amount of from 1 to 50 mg/ml, preferably from 1 to 20 mg/ml.

Examples of suitable organic solvents include toluene, xylene, acetone, aliphatic alcohols, benzene and ethyl acetate, which may usually be used in an amount of from 0.1 to 50 $\mu l$/ml, preferably from 1 to 20 $\mu l$/ml.

Both chemically pure and crude ascorbic acid or araboascorbic acid and phosphate donors other than ATP may be used for the purpose of the invention provided they contain ascorbic acid or araboascorbic acid or the phosphate donor and are not detrimental to AsA2P formation.

It is preferred to use ascorbic acid or araboascorbic acid and a phosphate donor other than ATP at concentrations of from 1 to 500mM and from 1 to 1000 mM, respectively.

In the second method, it is preferred to carry out the reaction at a temperature from 20° to 70° C. for a period of 1 to 48 hours, the pH being kept at 3 to 11 by the addition of, for example, ammonia, KOH or NaOH.

Examples of the products obtained by treatment of the culture broth include concentrated or dried culture broth, products obtained by adding a surfactant and/or organic solvent to the culture broth, products obtained by treating the cells with bacteriolytic enzyme, immobilized microbial cells and enzyme products extracted from the microbial cells.

The cells separated from the culture broth may preferably be used in an amount of from 1 to 400 mg/ml (wet cell weight).

It is possible to determine AsA2P quantitatively by measuring the absorption at 254 nm following high performance liquid chromatography through a Nucleosil 10C$_{18}$ column (commercial product of Masherey-Nagel, Japan) using a pure preparation of AsA2P obtained by chemical synthesis, as a reference.

Isolation of AsA2P from the culture broth or the reaction solution may be effected by removing the cells from the culture broth, where necessary removing proteins from the supernatant, neutralizing said supernatant and subsequently purifying the solution by column chromatography using, for example, ion-exchange resins, Sephadex or high performance liquid chromatography.

The following non-limiting examples illustrate the present invention.

EXAMPLE 1

Pseudomonas azotocolligans ATCC 12417 was cultured in KM102 medium (30 ml) at a temperature of 30° C. for 20 hours with rotation (220 r.p.m.) to obtain a seed. The seed (12 ml) was transferred to KM102 medium (300 ml) for culturing at a temperature of 30° C. for 20 hours with rotation (220 r.p.m.). The resultant culture broth was centrifuged (10,000 x g for 10 min.) to obtain wet cells (11.8 g) which were then freeze-dried at a temperature of −20° C. for preservation.

To a solution (50 ml) composed of ascorbic acid (200 mM), sodium acetate-buffered solution (100 mM), Nymin S-215 (4g/l; commercial product of Nihon Yushi K. K., Japan) and xylene (10 ml/1), a reaction solution (50 ml) containing the freeze-dried cells (50 mg/ml; calculated as wet cell weight) and one of the phosphate donors as shown in the following Table 1 ( 40 mM) were added.

The mixture was stirred (100 r.p.m.) with a magnetic stirrer for 10 hours whilst the pH was adjusted with caustic soda and/or hydrochloric acid, while the temperature was kept at 30° C.

The amount of the resultant AsA2P was measured by high performance liquid chromatography. Table 1 shows the relative activities thus obtained (compared to the activity obtained by the use of ATP) and the pH of the reaction solution.

TABLE 1

| Phosphate donor | Reaction pH | Relative activity (%) |
|---|---|---|
| Adenosine triphosphate | 5.48 | 100 |
| | 3.66 | 27 |

TABLE 1-continued

| Phosphate donor | Reaction pH | Relative activity (%) |
| --- | --- | --- |
| Acetylphosphoric acid | 5.68 | 66 |
|  | 3.88 | 103 |
| Paranitrophenyl phosphate | 5.97 | 89 |
|  | 3.76 | 90 |
| Pyrophosphoric acid | 4.62 | 94 |
|  | 4.07 | 127 |
| Tripolyphosphoric acid | 4.00 | 78 |
| Tetrapolyphosphoric acid | 4.00 | 66 |
| Polyphosphoric acid | 4.00 | 67 |
| Orthophosphoric acid | 4.00 | trace |

Notes: All reagents are commercial products of Nakarai Kagaku Kogyo K.K., Japan

EXAMPLE 2

Pseudomonas azotocolligans ATCC 12417 was cultured in KM102 medium (30 ml) at a temperature of 30° C. for 20 hours. The resultant seed (12 ml) was cultured at a temperature of 30° C. for 20 hours in KM102 medium (30 ml). The culture broth was centrifuged (10,000 X g for 10 minutes) to separate the wet cells (11.8 g) which were then frozen at a temperature of −20° C. for preservation. A reaction solution (50 ml) composed of frozen cells (50 mg/ml wet cells), ascorbic acid (200 mM), potassium pyrophosphate (200 mM), sodium acetate-buffered solution (pH 4.0; 100 mM), Nymin S-215 (4 g/1) and xylene (10 ml/1) was stirred (100 r.p.m.) for a period of 36 hours at 40° C. with a magnetic stirrer. The amount of AsA2P product was determined by high performance liquid chromatography.

It was noted that 32.0 mg/ml of AsA2P was present in the supernatant of the reaction solution at the end of the reaction and that the by-production of ascorbic acid-6-phosphate, ascorbic acid-3-phosphate and their pyrophosphates was substantially absent.

EXAMPLE 3

Each strain shown in Table 2 was cultured at a temperature of 30° C. for 20 hours in KM102 medium (30 ml). On each occasion, the resultant seed (12 ml) was transferred to KM102 medium (300 ml) for culturing at a temperature of 30° C. for 20 hours. Each fermented liquor thus-obtained was centrifuged (10,000 X g for 10 min.) to collect the microbial cells. The cells were freeze-dried and preserved at a temperature of −20° C. Then each reaction solution (50 ml) composed of the freezedried cells (50 mg/ml wet cell basis), ascorbic acid (200 mM), potassium pyrophosphate (200 mM), sodium acetate-buffered solution (pH 4.0; 100 mM), Nymin S-215 (4 g/1) and xylene (10 ml/1) was stirred for 24 hours with a magnetic stirrer, whilst the pH was adjusted to about 4.0 with NaOH and the temperature was kept at 30° C. After completion of the reaction, the amount of resultant AsA2P found in the supernatant of the reaction was determined by high performance liquid chromatography. The results are shown in Table 2.

TABLE 2

| Microorganism |  |  | AsA2P (g/l) |
| --- | --- | --- | --- |
| Klebsiella oxytoca | ATCC | 8724 | 0.53 |
| Cellulomonas flavigena SK-4 | FERM-BP | 1575 | 8.84 |
| Cellulomonas cartae | ATCC | 21681 | 8.13 |
| Alcaligenes eutrophus | ATCC | 17697 | 1.52 |
| Beneckea hyperoptica | ATCC | 15803 | 3.91 |
| Aeromonas hydrophila | ATCC | 11163 | 3.82 |
| Klebsiella pneumoniae | ATCC | 21525 | 0.60 |
| Brevibacterium lyticum | ATCC | 15921 | 0.92 |
| Brevibacterium ammoniagenes | ATCC | 6872 | 0.37 |
| Brevibacterium flavum | ATCC | 13826 | 0.28 |
| Brevibacterium lactofermentum | ATCC | 13655 | 0.44 |
| Pseudomonas riboflavina | ATCC | *9526 | 8.89 |
| Pseudomonas diminuta | ATCC | 11568 | 1.01 |
| Flavobacterium devorans | ATCC | 10829 | 1.74 |
| Pseudomonas maltophilia | ATCC | 17806 | 2.19 |
| Xanthomonas oryzae | IFO | 3995 | 0.27 |
| Morganella morganii | ATCC | 25830 | 1.04 |
| Serratia rubidaea | ATCC | 11634 | 0.20 |
| Enterobacter aerogenes | ATCC | 13048 | 0.23 |
| Bacillus subtilis | ATCC | 19221 | 2.54 |
| Corynebacterium glutamicum | ATCC | 13032 | 0.40 |

EXAMPLE 4

Pseudomonas azotocolligans ATCC 12417 was cultured at a temperature of 30° C. for 20 hours in KM102 medium (30 ml) with rotation (220 r.p.m.) to obtain a seed, which (12 ml) was transferred to KM102 medium (300 ml) for culturing at a temperature of 30° C. for 20 hours with rotation (220 r.p.m.).

The resultant culture broth was adjusted to a pH of 4.0 with hydrochloric acid, after addition of ascorbic acid (200 mM), Nymin S-215 (4 g/l), xylene (10 ml/l) and pyrophosphoric acid (40 mM), and then the reaction solution was stirred (100 r.p.m.) at 30° C. for 10 hours to complete the reaction. 8.82 g/l of AsA2P was found in the reaction solution.

EXAMPLE 5

In a similar manner to that described in Example 1, Pseudomonas azotocolligans ATCC 12471 was cultured. The cultured cells were frozen at a temperature of −20° C. After addition of Nymin S-215 (4 g/l) and xylene (10 ml/l), the frozen cells are heated to a temperature of 30° C. for 10 minutes. These cells were then added to araboascorbic acid (200 mM) and one of the phosphate donors as shown in the following Table 3 (150 mM) in sodium acetate-buffered solution (pH 4.0; 40 mM), in an amount of 50 mg/ml (on the basis of the weight of wet cells). The reaction was effected for 60 minutes. During the reaction, the reaction solution was stirred with a magnetic stirrer (100 r.p.m.), the pH of the solution was adjusted to about 4.0 with NaOH. The reaction temperature was kept at 30° C. After completion of the reaction, high performance liquid chromatography was applied to measure the amount of AsA2P formed in the supernatant of the reaction solution. The results are shown in Table 3:

TABLE 3

| Phosphate donor | AsA2P (g/l) |
| --- | --- |
| pyrophosphoric acid | 1.56 |
| tripolyphosphoric acid | 1.14 |
| tetrapolyphosphoric acid | 1.05 |
| acetylphosphoric acid | 2.00 |
| p-nitrophenylphosphoric acid | 1.53 |
| adenosine triphosphate | 0.30 |
| adenosine triphosphate (pH 5.5) | 1.37 |

We claim:

1. A process for the preparation of ascorbic acid-2-phosphate, which comprises the steps of reacting ascorbic acid with a phosphate donor other than ATP in an aqueous medium in the presence of an effective amount of an enzyme derived from a culture of a microorganism capable of preferentially catalyzing the enzymatic phosphorylation at the 2-position of said ascorbic acid by said phosphate donor, and then recovering the resultant ascorbic acid-2-phosphate from the reaction solution, wherein said microorganism is chosen from the group consisting of Klebsiella oxytoca, ATCC 8724;
Cellumonas cartai, ATCC 21681;
Alcaligenes eutrophus, ATCC 17697
Beneckea hyperoptica, ATCC 15803;
Aeromonas hydrophila, ATCC 11163;
Klebsiella pneumoniae, ATCC 21524;
Brevibacterium lyticum, ATCC 15921;
Brevibacterium ammoniagenes, ATCC 6872;
Brevibacterium flavum, ATCC 13826;
Brevibacterium lactofermentum, ATCC 13655;
Pseudomonas riboflavina, ATCC 9526;
Pseudomonas diminuta, ATCC 11568;
Flavobacterium devorans, ATCC 10829;
Pseudomonas azotocolligans, ATCC 12417
Pseudomonas maltophilia, ATCC 17806;
Morganella morganii, ATCC 25830;
Serratia rubidaea, ATCC 11634;
Enterobacter aerogenes, ATCC 13048; and
Corynebacterium glutamicum, ATCC 13032.

2. The process according to claim 1, wherein said phosphate donor is selected from the group consisting of non-nucleoside phosphate esters, acetyl phosphoric acid and mixtures thereof.

3. The process according to claim 1, wherein said phosphate donor is selected form the group consisting of substituted phenyl phosphates and acetyl phosphoric acid.

4. The process according to claim 1, wherein said phosphate donor is selected from the group consisting of paranitrophenylphosphate, acetylphosphoric acid, pyrophosphoric acid, tripolyphosphoric acid, tetrapolyphosphoric acid and polyphosphoric acid.

5. The process according to claim 1, wherein the enzymatic reaction is effected in the culture broth of said enzyme-producing microorganism.

6. The process according to claim 5, wherein said broth culturing is effected at a temperature ranging from between about 20° to 40° C., at a pH between about 4 and 10 and for a period of form about 1 to 100 hours, in the presence of ascorbic acid and an effective amount of said phosphate donor.

7. The process according to claim 1, wherein the enzymatic reaction is effected by contacting said ascorbic acid with a phosphate donor other than ATP in the presence of a catalyzing amount of at least one member selected from enzymatic sources selected from the group consisting of concentrated culture broths, dried culture broths, supernatants of said culture broths, microbial cells of catalyzing cultures treated with a bacteriolytic enzymes, immobilized enzymes and enzymes extracted form the microbial cell cultures.

8. A process according to claim 7, wherein the enzymatic reaction is effected at a temperature of from about 20° to 70° C. at a pH of from about 3 to 11; for a period of from about 1 to 48 hours.

* * * * *